(12) United States Patent
Maekawa

(10) Patent No.: US 6,908,753 B1
(45) Date of Patent: Jun. 21, 2005

(54) TRACE ELEMENT-CONTAINING CARRIER FOR GROWING MICROORGANISM

(75) Inventor: Takaaki Maekawa, Tsukuba (JP)

(73) Assignee: Japan Science and Technology Corporation, Saitama (JP)

(*) Notice: Subject to any disclaimer, the term of this patent is extended or adjusted under 35 U.S.C. 154(b) by 0 days.

(21) Appl. No.: 10/069,796

(22) PCT Filed: Oct. 19, 1999

(86) PCT No.: PCT/JP99/05758
§ 371 (c)(1), (2), (4) Date: May 20, 2002

(87) PCT Pub. No.: WO01/29203
PCT Pub. Date: Apr. 26, 2001

(51) Int. Cl.⁷ .................. C12N 11/14; C12N 11/02; C12N 11/08; C12N 1/20; C12M 1/00
(52) U.S. Cl. .................. 435/176; 435/177; 435/180; 435/253.6; 435/289.1
(58) Field of Search ................. 435/174, 177, 435/180, 178, 395, 243, 253.6, 289.1

(56) References Cited

FOREIGN PATENT DOCUMENTS

| JP | 58-31987 | 2/1983 |
|---|---|---|
| JP | 1-171643 | 7/1989 |
| JP | 2-131578 | 5/1990 |
| JP | 5-76365 | 3/1993 |
| JP | 6-207071 | 7/1994 |
| JP | 9-275981 | 10/1997 |
| JP | 11-123076 | 5/1999 |

*Primary Examiner*—David M. Naff
(74) *Attorney, Agent, or Firm*—Wenderoth, Lind & Ponack, L.L.P.

(57) ABSTRACT

Provided is a bacteria culture carrier in which a polymer product having a trace element and an inorganic nutrient salt for growth of bacteria included therein is laminated by being held with an inorganic porous material. This carrier is useful in a bioreactor or wastewater disposal with a high activity and a high density of bacteria.

3 Claims, 9 Drawing Sheets

(A)

(B)

TRACE ELEMENT-CONTAINING CARRIER FOR GROWING MICROORGANISM

FIELD OF THE INVENTION

The present invention relates to a trace element/inorganic nutrient salt diffusion-type bacteria culture carrier. More specifically, the invention relates to a trace element/inorganic nutrient salt diffusion-type bacteria culture carrier which is useful in a wastewater disposal apparatus, a food-making industry and a drug-producing industry.

BACKGROUND OF THE INVENTION

As a method for producing a carrier, a method in which bacteria or enzymes are included in a polymer gel (inclusion method) has been so far known, and it has been industrially utilized.

However, the ordinary method depends on a phenomenon that trace metal elements or inorganic nutrient salts useful for growth of bacteria are diffused and moved from an external culture solution to the inside of a carrier. Accordingly, a diffusion rate of these materials is controlled by the growth of bacteria. Further, since a metabolized substance has resistance to diffusion onto a surface of a carrier, which sometimes hinder the growth of bacteria. Still further, when a gaseous substance is metabolized, floating or destruction of a carrier occurs. Furthermore, in the ordinary method such as the inclusion method, the activity of bacteria is notably decreased owing to toxicity of a polymer used. Therefore, even when a density of bacteria is increased, the activity thereof is not necessarily proportional to the density of bacteria. These are the problems of the ordinary method.

In order to solve these problems, a surface-binding-type carrier was developed in which bacteria and the carrier are physicochemically adhered.

Nevertheless, since this method depends on the physicochemical adhesion between a viscous polymeric substance secreted in the growth of bacteria and the carrier, the growth of bacteria is controlled by the composition of inorganic nutrient salts or trace elements of a liquid entered from an external solution. Moreover, it involves problems that when bacteria present on a surface of a carrier flow within a bioreactor, peeling of bacteria occurs and high-density enrichment culture is naturally restricted.

SUMMARY OF THE INVENTION

Under these circumstances, the invention aims to provide a novel trace element/inorganic nutrient salt diffusion-type bacteria culture carrier in which a high activity and a high density of bacteria can be realized in a bioreactor or a wastewater disposal apparatus.

The invention is to provide, upon solving the problems, a bacteria growth carrier including a trace element in which an element polymer product obtained by including a trace element for growth of bacteria in a synthetic or natural polymeric material is laminated by being held with a synthetic or natural inorganic porous material.

Further, the invention is to provide the bacteria growth carrier which is a particulate, cylindrical or plate-like carrier, or the bacteria growth carrier which has a honeycomb structure.

DETAILED DESCRIPTION OF THE INVENTION

Figure 1:
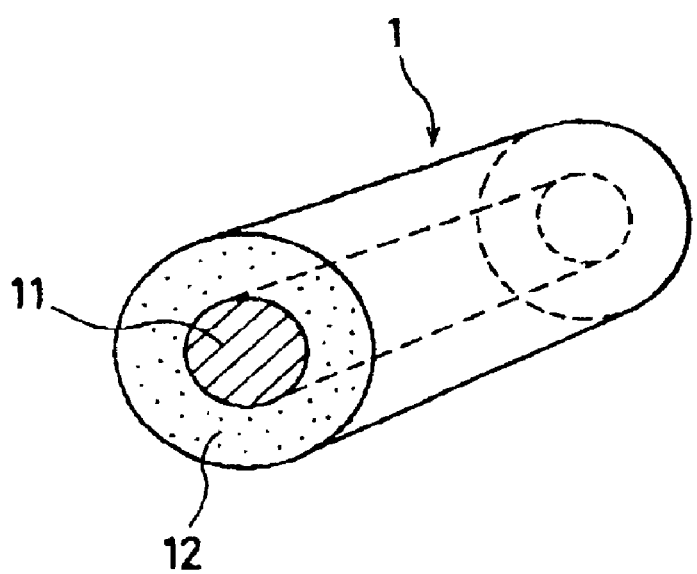
FIG. 1 is a perspective view showing a cylindrical carrier of the invention.

In the invention, as the binding-type carrier, a useful substance such as a trace metal element or an inorganic nutrient salt required for growth of bacteria is included at a high concentration in a synthetic or natural polymeric substance within a binding-type carrier. And, a porous material (a synthetic or natural inorganic porous material) in which microorganisms can easily live are mounted therearound to increase the living density of microorganisms.

Such a carrier is installed in a reactor. Around the carrier, a liquid to be treated is contacted with a group of microorganisms in a stream parallel or perpendicular to the carrier to degrade a substrate.

Consequently, the decrease in activity of bacteria due to toxicity of a polymeric material to be used is prevented. Further, inhibition of growth is prevented by adjusting a thickness of a polymer product or an inorganic porous material constituting a carrier and a pore of the inorganic porous material. Still further, physiological peeling of bacteria is prevented according to types and characteristics of bacteria and fluidity of a reactor to be used.

Moreover, the invention is also based on the finding in studies on culture of methane bacteria at high concentrations, that is, a density of bacteria can be increased in view of the knowledge that the growth of bacteria is controlled by deficiency of a trace element or an inorganic nutrient salt required for growth of bacteria.

In addition, this finding agrees with the minimum law of Liebig that when only one of substances required for bacteria is deficient, growth of any bacteria is stopped. From this finding, in a method for feeding substances required for growth of various bacteria acting in a bioreactor or a wastewater disposal apparatus, these substances are included at high concentrations inside a carrier, and moved from the inside to the surface of the carrier by diffusion to supply the same to bacteria living on the surface thereof. Bacteria digest the substances to continue the growth, whereby the high density of bacteria can be maintained. This has been also identified by experiments.

With respect to the polymeric material of the invention including a trace element or an inorganic nutrient salt, typical examples of a synthetic polymeric material are polymers known as water-absorbable polymers, such as an acrylic polymer, a methacrylic polymer, a vinyl alcohol polymer, a vinyl ester polymer, a polyether, a polyester and a polyolefin polymer, copolymers thereof, and gels thereof. A trace element or an inorganic nutrient salt is included and immobilized in these polymeric materials. The polymeric material may be formed as an agglomerate of a finely divided polymer.

Further, a polymeric material may be a natural polymeric material. It may include various materials such as an agar gel, celluloses and polysaccharides.

The inorganic porous material of the invention may include various synthetic or natural porous materials. Ceramics, porous concretes and volcanic porous materials such as rock wool and pumice are available. When the porosity is slightly less than 95% or 95 to 98% including an approximate range slightly exceeding 98%, preferably 95 to 98% and a diameter of the pore is 2 to 0.1 mm, the porous material is most suitable for growth of bacteria. Further, it is required to select a porous material which does not elute a substance (heavy metal such as Cd) harmful for growth of bacteria used. Moreover, it is important to select a natural porous material which is not easily degraded with anaerobic bacteria.

The element polymer product including the trace element and the inorganic nutrient salt is, in the carrier of the invention, laminated by being held with the inorganic porous material. The whole carrier may take various shapes. Examples thereof can include a cylindrical carrier, a rectangular carrier, a flat-plate-like carrier and a curved-plate-like carrier.

The trace element and the inorganic nutrient salt in the invention may be selected from trace metal elements and inorganic nutrient salts ordinarily considered. Examples of the trace element include Mg, Mn, Fe, Ni, Co, Cu, Se, Mo, Al, W, Ca and B. Examples of the inorganic nutrient salt include a phosphate and a carbonate of an alkali metal.

Bacteria themselves are bound and immobilized, for example, on the surface, in the inner pores or in the voids of the porous material through covalent bond, physical adsorption or ionic bond. Bacteria may previously be included in the carrier, laminated on the surface of the carrier, or both included therein and laminated thereon, depending on characteristics of the carrier.

The drawings appended illustrates the carrier of the invention. FIG. 1 shows a cylindrical carrier 1. A polymer product 11 as a core includes a trace element and an inorganic nutrient salt for growth of bacteria. This core has a structure that it is laminated by being hold with a surrounding inorganic porous material 12.

Figure 2:
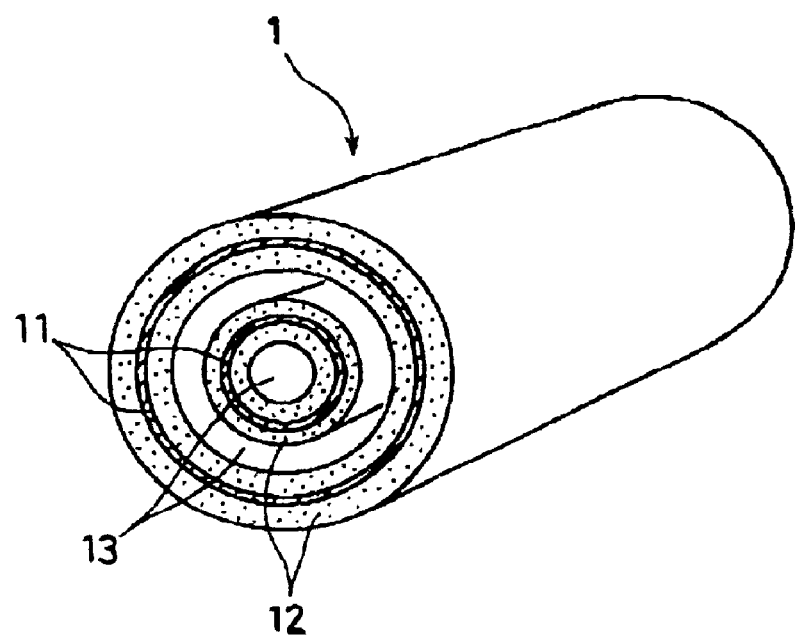
FIG. 2 is a perspective view showing a multiple cylindrical carrier.

FIG. 2 shows a multiple cylindrical carrier 1. In this case, a cylinder having a hollow portion 13 has a structure that a polymer product 11 including a trace element and a nutrient salt for growth of bacteria is laminated by being held with the inorganic porous materials 12.

Figure 3:
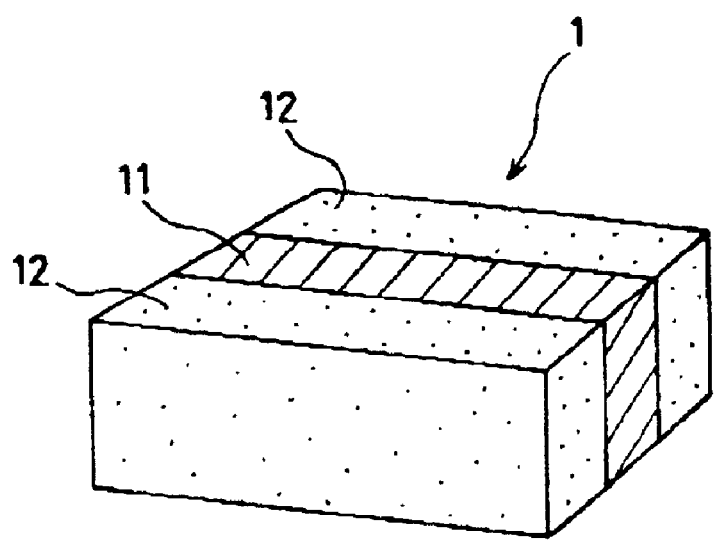
FIG. 3 is a perspective view showing a flat-plate-like carrier.

FIG. 3 shows a flat-plate-like carrier 1. This carrier has a structure that the flat-plate-like polymer product 11 is laminated by being held with the inorganic porous materials 12.

Figure 4:
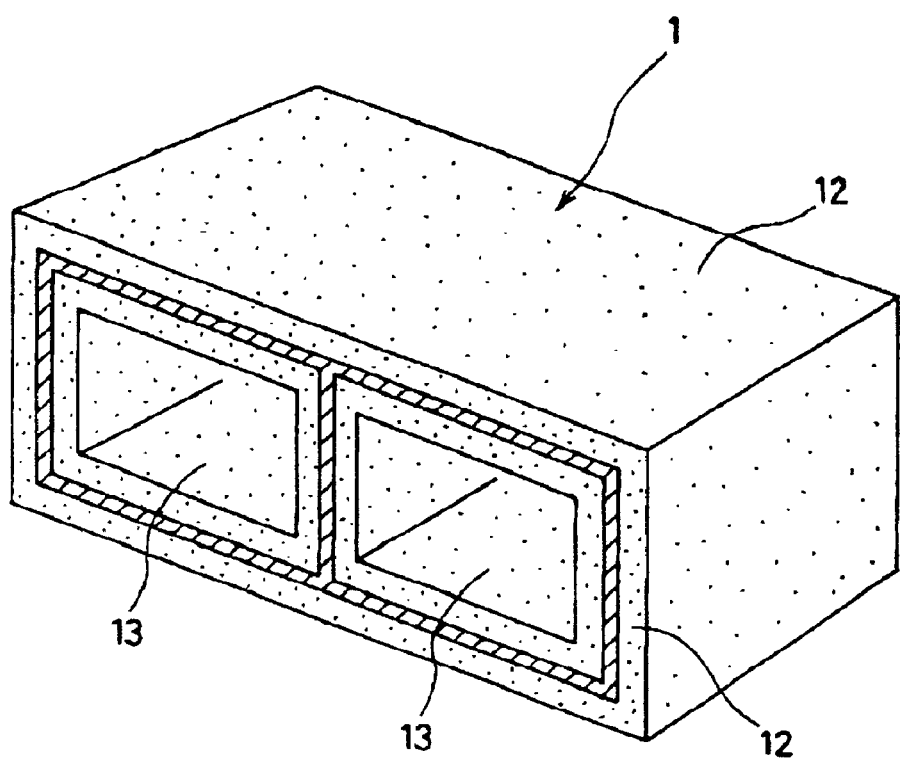
FIG. 4 is a perspective view showing a part of a carrier of honeycomb structure.

FIG. 4 shows a carrier 1 of a honeycomb structure. On a wall surface surrounding a hollow portion 13, the polymer product 11 as above described is laminated by being held with the inorganic porous materials 12.

Such a carrier is installed in, for example, a bioreactor. In the application to the bioreactor, the carrier and its arrangement can be determined in consideration of a purpose of culture, types and properties of bacteria, a substrate and a diffusion rate of a trace element and an inorganic nutrient salt to conduct the culture most efficiently in relation to a liquid flow in the bioreactor.

Figure 5:
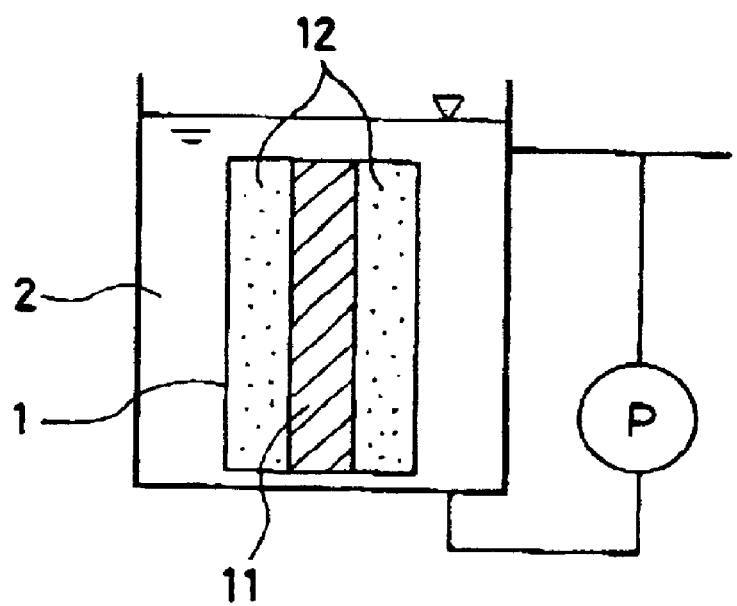
FIG. 5 is a sectional view showing an example in which the carrier of the invention is installed in a bioreactor.
Figure 6:
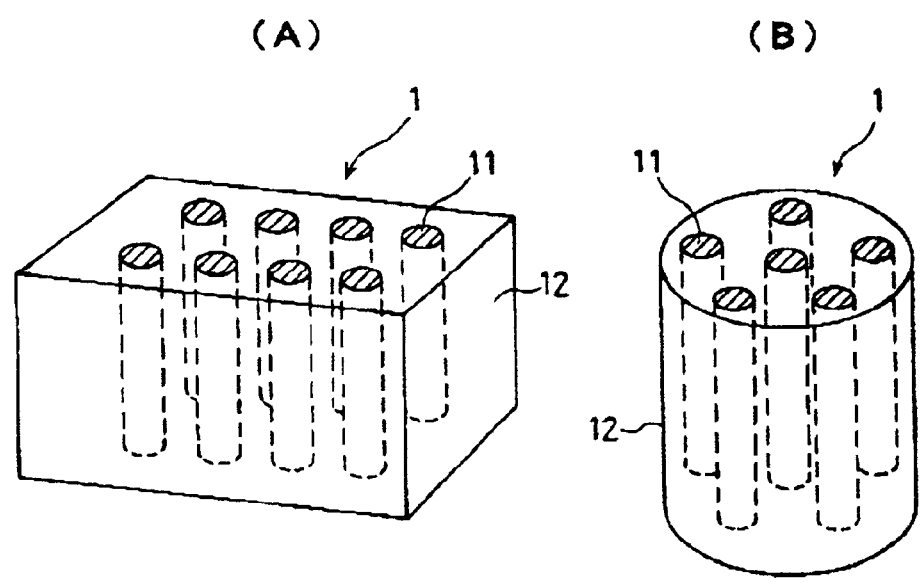
FIGS. 6A and 6B are perspective views showing carriers in which plural holes are formed in rectangular and cylindrical porous materials and polymer products are packed therein.
Figure 7:
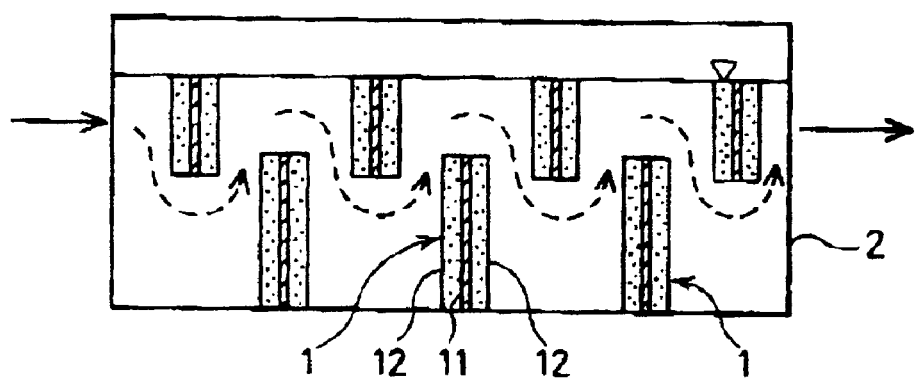
FIGS. 7A and 7B are a side sectional view and a plan view each showing an example in which carriers are installed in a bioreactor.
Figure 7:
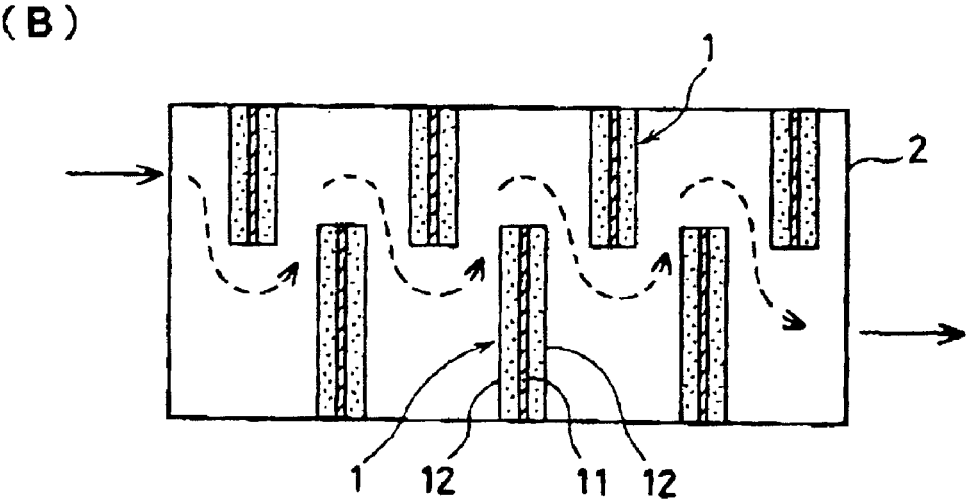
Figure 8:
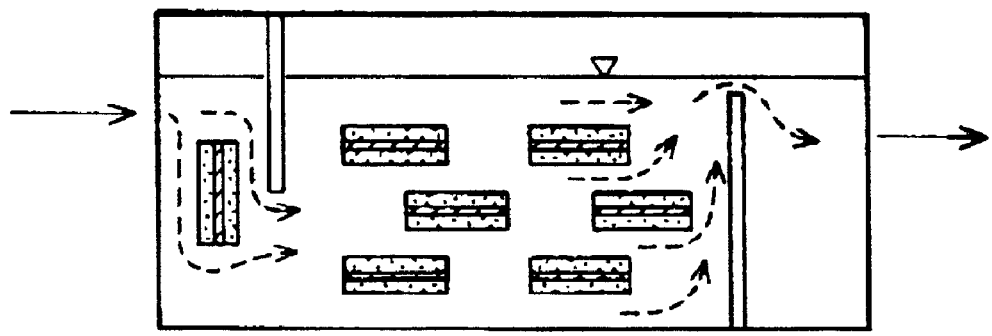
FIG. 8 is a sectional view showing an example in which carriers are installed in parallel to a flow within a bioreactor.
Figure 9:
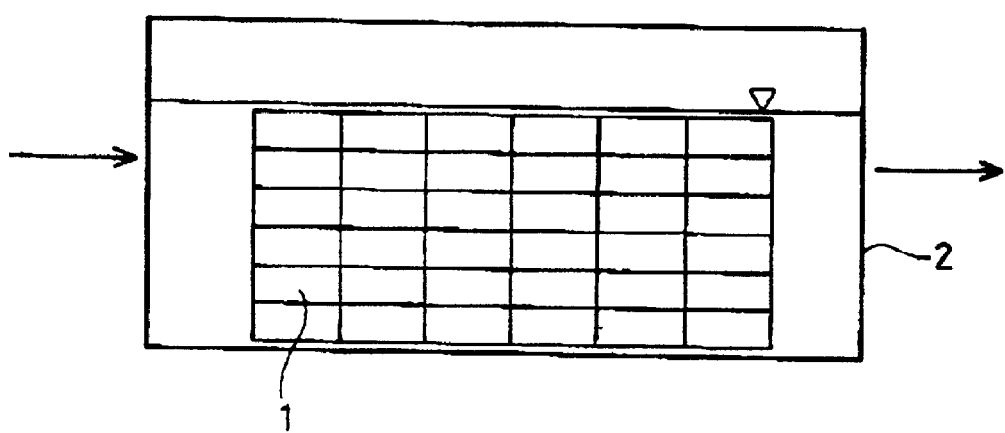
FIGS. 9 is a sectional view showing an example in which carriers in FIG. 3, 4 or 6A are installed.

For example, FIG. 5 shows an example in which the carrier 1 in FIGS. 1 to 3 is installed in the reactor 2, and FIGS. 6A and 6B show examples in which plural holes are formed approximately in parallel in the rectangular and cylindrical inorganic porous materials 12 and cylindrical and particulate polymer products 11 including trace elements and inorganic nutrient salts are packed in the holes. In FIG. 7, for example, the flat-plate-like carriers 1 in FIG. 3 are mounted within the reactor 2 in zigzag state vertically and horizontally to control the flow as shown in a side sectional view of FIG. 7A and a plan view of FIG. 7B. FIG. 8 shows an example in which the carriers 1 in FIGS. 1 to 3 are installed such that the side portion of the inorganic porous material 2 is approximately parallel to a flow direction of a culture solution. FIG. 9 shows a structure in which the carriers 1 in FIG. 3, FIG. 4 and FIG. 6A are laminated in a bioreactor. In this case, the side surface is approximately parallel to the flow. In the embodiment of FIG. 9, it is identified that an excellent performance is exhibited by making a packing rate of the polymer products 15 to 25% (volume percentage) of an effective volume.

When the carrier of the invention is used, for example, 10 to 25 g dry cells/liter can be expected as a cell concentration. In the ordinary method, it was approximately 1 to 5 g dry cells/liter.

Further, when an amount of a substrate in a degradation system in wastewater disposal is represented by S, the degradation thereof is represented by the formula:

$$\left(\frac{dS}{dt}\right) = -\mu \cdot X / Y_{x/s}$$

wherein $\mu$ represents a specific growth rate of bacteria, X represents a density of bacteria, and $Y_{x/s}$ represents a yield of bacteria (which is a fixed value depending on bacteria).

In the invention, the reactor is operable when $\mu$ is close to $\mu_{max}$, whereby the density x of bacteria can be increased by 2 to 10 times in comparison with that in an ordinary reactor. Accordingly, a degradation rate of a suspension culture apparatus is increased by 2 to 10 times in comparison with that in an ordinary apparatus. It can be increased by several times in comparison with that in a bioreactor using an ordinary carrier.

The invention is now described in more detail by referring to the following Example.

EXAMPLE

A trace element and a metal salt as an inorganic nutrient salt were supported on a PVA (polyvinyl alcohol) polymer gel obtained by dissolving approximately 16% by weight of a polymeric material having a weight average molecular weight of approximately 2,000 and a saponification degree of 98% in water and crosslinking the solution with saturated boric acid. The resulting polymer product was filled in six holes of rock wool as an inorganic porous material so as to provide a cylindrical shape shown in FIG. 6B. Methane bacteria were incubated such that the volume of the polymeric material filled in the carrier corresponded to 20% of a liquid portion. This was compared with a case in which a carrier was not used. The liquid temperature was set at 5° C., 15° C. and 25° C.

Table 1 shows a trace metal element, Table 2 a basic inorganic salt, and Table 3 a composition of a vitamin solution respectively.

Further, Table 4 shows physical properties and a composition of rock wool as an inorganic porous material.

TABLE 1

| Component | Concentration (µg/liter) |
|---|---|
| $MgCl.6H_2O$ | 410 |
| $MnCl.4H_2O$ | 50 |
| $FeCl_2.4H_2O$ | 50 |
| $NiCl_2.6H_2O$ | 12 |
| $ZnSO_4.7H_2O$ | 10 |
| $CoCl_2.6H_2O$ | 10 |
| $CaCl_2.2H_2O$ | 10 |
| $Na_2.SeO_3$ | 8 |
| $Na_2MoO_4.2H_2O$ | 2.4 |
| $CuSO_4.5H_2O$ | 1 |
| $AlK(SO_4)_2$ | 1 |
| $H_3BO_3$ | 1.8 |
| $NaWO_4.2H_2O$ | 1 |

TABLE 2

| Component | Concentration (mg/liter) |
|---|---|
| $KH_2PO_4$ | 3400 |
| $K_2HPO_4$ | 3400 |
| $NH_4Cl$ | 2130 |
| $Na_2CO_3$ | 2540 |
| Resazurin | 2 |

TABLE 3

| Component | Concentration (µg/liter) |
|---|---|
| Biotin | 20 |
| Folic acid | 20 |
| Pyridoxine hydrochloride | 20 |
| Thiamine hydrochloride | 100 |
| Riboflavin | 50 |
| Nicotinic acid | 50 |
| Calcium DL-pantothenate | 50 |
| p-Aminobenzoic acid | 50 |
| Lipoic acid | 50 |

TABLE 4

| Physical properties and composition of rock wool | |
|---|---|
| Density (kg/m³) | 80 ± 12 |
| True specific gravity | 2.9 |
| Porosity (%) | 95–98 |
| Composition (%) | $SiO_2$: 42, $Al_2O_3$: 15, CaO: 33, MgO: 6, Fe: 0.5, $TiO_2$: 0.9, MnO: 0.2, $Na_2O$: 1, $K_2O$: 0.8 |

The incubation of methane bacteria at various incubation temperatures was compared with that in the absence of a carrier. As a result, with respect to amounts of methane bacteria and a methane production rate, the results shown in Table 5 were obtained.

TABLE 5

| Temperature (° C.) | Amounts of methane bacteria | Methane production rate |
|---|---|---|
| 25 | 4.8 times | 5.8 times |
| 15 | 2.5 times | 5.1 times |
| 5 | 2.3 times | 4.5 times |

In Table 5, concentrations of a trace element and an inorganic nutrient salt in a carrier were 1,000 times as high as those in an ordinary method. It has been identified that with respect to the polymer product and the inorganic porous material charged into a reactor, it is mainly the volume of the polymer product and the porosity of the inorganic porous material that influence the incubation. However, when a porosity is 95 to 98%, an apparent volume of the porous material is almost unchanged.

When the carrier takes the shape in FIG. 5, it is estimated that the upper limit of the volume of the polymer product is approximately 25% of a liquid volume.

As is clear from Table 5, compared with the absence of the carrier, the presence of the carrier provides the excellent effects that the amounts of methane bacteria are 2.3 to 4.8 times and the methane production rate is 4.5 to 5.8 times. Consequently, it is considered that the same excellent results can bed obtained in a model plug flow-type bioreactor shown in FIGS. 7 to 9 as well. Therefore, as an application to an actual biosystem, a test was conducted with nitrifying and denitrifying bacteria such that a carrier of FIG. 6A provided by incorporating the polymer products in a porous concrete block was mounted on a bottom of a sewage treatment channel. As a result, removal rates of 50 to 60% and 40 to 50% (annual average) could be attained in T-N and T-P, respectively.

As has been thus far described in detail, the invention can provide a novel trace element/inorganic nutrient salt diffusion-type bacteria culture carrier in which a high activity and a high density of bacteria can be realized in a bioreactor or a wastewater disposal apparatus. Further, the use of this carrier in environmental conservation of a biosystem can help to repair polluted environment or improve a rate of repair.

What is claimed is:

1. A bacteria growth carrier including a trace element wherein a polymer product obtained by including a trace element or the trace element and an inorganic nutrient salt for growth of bacteria in a synthetic or natural polymeric material is held between layers of a synthetic or natural inorganic porous material.

2. The bacteria growth carrier as claimed in claim 1, which is a particulate, cylindrical or plate-like carrier.

3. The bacteria growth carrier as claimed in claim 1, which has a honeycomb structure.

* * * * *